(12) United States Patent
Gabriel et al.

(10) Patent No.: US 6,203,529 B1
(45) Date of Patent: Mar. 20, 2001

(54) NEEDLE ARRANGEMENT

(75) Inventors: Jochen Gabriel, Stuttgart; Ulf Polzin, Leinfelden, both of (DE)

(73) Assignee: B D Medico, Mies (CH)

(*) Notice: Subject to any disclaimer, the term of this patent is extended or adjusted under 35 U.S.C. 154(b) by 0 days.

(21) Appl. No.: 09/530,894

(22) PCT Filed: Nov. 11, 1998

(86) PCT No.: PCT/EP98/07230
§ 371 Date: May 4, 2000
§ 102(e) Date: May 4, 2000

(87) PCT Pub. No.: WO99/25402
PCT Pub. Date: May 27, 1999

(30) Foreign Application Priority Data

Nov. 19, 1997 (DE) .......................................... 297 20 513 U (51) Int. Cl.$^7$ .................................................. A61M 5/00
(52) U.S. Cl. ........................... 604/192; 604/198; 604/263
(58) Field of Search .................................. 604/192, 198, 604/110, 187, 263

(56) References Cited

U.S. PATENT DOCUMENTS

| | | | |
|---|---|---|---|
| 2,876,770 | 3/1959 | White | 128/215 |
| 5,292,314 | 3/1994 | D'Alessio et al. | 604/198 |
| 5,403,286 | 4/1995 | Lockwood, Jr. | 604/110 |
| 5,429,612 | 7/1995 | Berthier | 604/198 |
| 5,578,014 | 11/1996 | Erez et al. | 604/192 |
| 5,658,256 | 8/1997 | Shields | 604/192 |

FOREIGN PATENT DOCUMENTS

| | | |
|---|---|---|
| 89 09 799 U | 11/1989 | (DE) . |
| 691 08 928 T2 | 11/1995 | (DE) . |
| 196 00 058 A1 | 7/1997 | (DE) . |
| 0 182 682 | 5/1986 | (EP) . |
| 0 405 039 A1 | 1/1991 | (EP) . |
| 0 520 930 A1 | 12/1992 | (EP) . |
| 0 749 758 A1 | 12/1996 | (EP) . |
| 93 01153 | 8/1994 | (FR) . |
| WO91-13643 | 9/1991 | (WO) . |
| WO93-05835 | 4/1993 | (WO) . |
| WO94-03220 | 2/1994 | (WO) . |
| WO94-04205 | 3/1994 | (WO) . |

*Primary Examiner*—John D. Yasko
(74) *Attorney, Agent, or Firm*—Milton Oliver; Ware, Fressola, Van Der Sluys & Adolphson LLP (57) ABSTRACT

The invention concerns a needle arrangement for an injection device (16). It has a hollow needle carrier (10) on which a hollow needle (12) is mounted and which is configured for mounting on the injection device (16). The arrangement has a cap (32) which is displaceable on the hollow needle carrier (10) approximately parallel to the longitudinal extension of the hollow needle (12), is equipped at its proximal end segment with a passthrough opening (42) for the hollow needle (12), and in its proximal end position substantially conceals the hollow needle (12). A compression spring (26) is arranged between the hollow needle carrier (10) and cap (32) in order to displace the cap (32) into its proximal end position. Also provided is a covering cap (66) which surrounds the displaceable cap (32), the hollow needle (12), and the hollow needle carrier (10), and is sealed on its open side by a sealing member (71) that is removable by the user. A needle arrangement of this kind can easily be replaced after an injection. It improves compliance because the patient does not at any time see the hollow needle (12). The compression spring can be configured as a plastic spring (26). It is preferably integral with the hollow needle carrier (10), which simplifies manufacture.

16 Claims, 7 Drawing Sheets

NEEDLE ARRANGEMENT

FIELD OF THE INVENTION

The invention relates to a needle arrangement for an injection device.

BACKGROUND

A needle arrangement of this kind is known from EP 0 749 758 A1, HJERTMAN et al. In it, a hollow needle that is mounted on a hollow needle holder is used. The latter is screwed onto an external thread at the proximal end of the injection device. A special apparatus which makes the hollow needle invisible to the user, so as to eliminate his or her anxiety regarding injections, is then slid over this hollow needle.

SUMMARY OF THE INVENTION

It is the object of the invention to make available a new needle arrangement for an injection device.

According to the invention, this object is achieved by providing a compressible spring surrounding the needle, and a generally cylindrical open-ended first cap which fits over the spring.

A needle arrangement of this kind is very easy to utilize, since in practice it uses nothing more than a replaceable hollow needle. Easy adjustment of the penetration depth is also achieved, since the necessary penetration depth may be different depending on the patient's constitution. In this instance, it can be adjusted easily and obviously.

Another manner of achieving the stated object is to make the spring of plastic material, and form it integrally with a hollow needle carrier.

An arrangement of this kind has only a few parts and thus can be produced very economically. It can be used by the patient in a simple, easily understandable fashion.

A further manner of achieving the stated object is to provide a second covering cap which surrounds the first cap, the needle, and the needle carrier, and is sealed closed by a peelable foil, thereby keeping the surrounded elements sterile until the user peels off the foil.

A needle arrangement of this kind can very easily be kept sterile until used. The covering cap is usable as an assembly aid, additionally facilitating use by the patient.

Each time the patient thrusts the hollow needle in prior to an injection, the displaceable cap is displaced in the distal direction against the force of the spring, and when the hollow needle is pulled out it moves back into its proximal end position under the action of the spring, so that the patient does not see the hollow needle during the entire injection procedure. Because of the detachable mounting on the injection device, a needle arrangement of this kind can very easily be replaced, after an injection, with a new, sterile needle arrangement.

BRIEF FIGURE DESCRIPTION

Further details and advantageous developments of the invention are evident from the exemplary embodiment, which is described below and depicted in the drawings and is in no way to be understood as a limitation of the invention, and from the dependent claims. In the drawings:

DETAILED DESCRIPTION

In the description that follows, the terms "proximal" and "distal" will be used in the manner usual in medicine, to wit:

"Proximal"=facing toward the patient (the end of the injection device having the needle);

"distal"=facing away from the patient.

Figure 1:
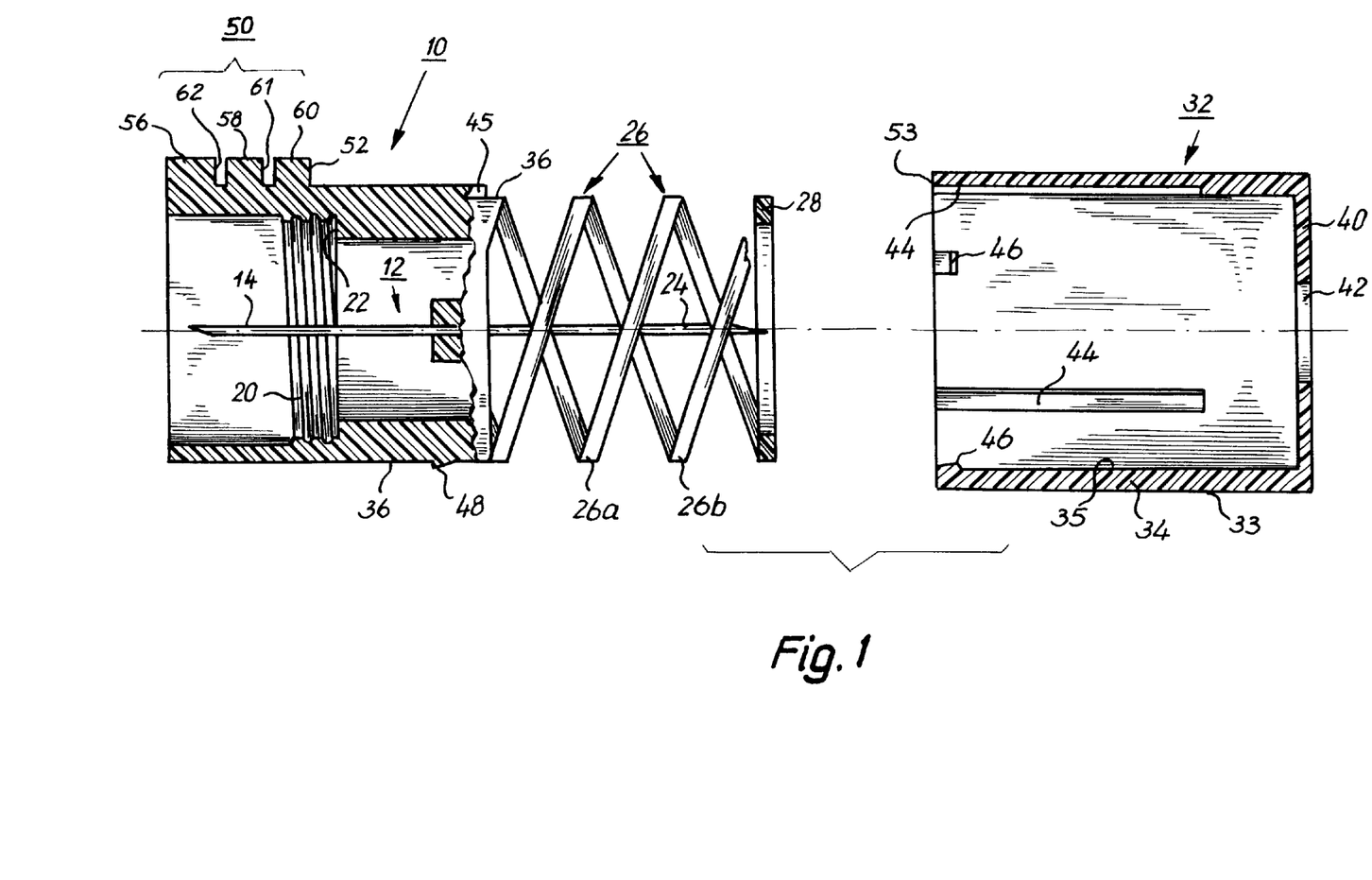
FIG. 1 is a longitudinal section through a preferred embodiment of a needle arrangement according to the present invention, in an exploded and greatly magnified depiction.

FIG. 1 shows, on the left, a hollow needle carrier 10 made of a suitable plastic, e.g. polyethylene. Secured in this is a hollow needle (injection needle) 12 whose distal end 14 serves to pierce through the rubber membrane (not depicted) on the reservoir of an injection device 16 that is indicated only schematically in FIGS. 2 and 3.

An inner thread 20 of hollow needle 10, which is delimited in the proximal direction by a shoulder 22 serving as a stop, provides detachable mounting on an external thread 18 at the proximal end of injection device 16.

The proximal segment of hollow needle 12 is labeled 24. Extending concentrically around it, in the arrangement as shown in FIG. 1, is a plastic spring 26 that can be configured integrally with hollow needle carrier 10 and that here comprises two helical springs or spirals 26a, 26b, offset 180°, which each transition at their proximal end into a ring 28 with which they can also be integrally configured. Alternatively a separate spring, for example made of metal, could also be used here.

A first sleeve or cap 32 has a substantially cylindrical segment 34 whose cylindrical outer side is labeled 33 and whose cylindrical inner side 35 is configured for sliding displacement on the (also cylindrical) circumference 36 of hollow needle carrier 10. First cap 32 furthermore has at proximal end a base 40 in whose center is located a recess 42 through which proximal end 24 of hollow needle 12 can pass during an injection, as shown in FIG. 3.

First cap 32 has on its inner side 35 a total of three longitudinal grooves 44, only two of which are visible in FIG. 1, uniformly distributed on the circumference and providing axial guidance, i.e. rotation prevention. They coact with three projections 45, complementary thereto, on the cylindrical outer circumference 36 of hollow needle carrier 10, as clearly shown by FIGS. 2 and 3.

First cap 32 furthermore has three barbs 46 on its inner circumference 35. These barbs are also uniformly distributed on the circumference, and coact with three corresponding complementary barbs 48 on outer circumference 36 of hollow needle 10, only one of which is visible in FIG. 1. During assembly, barbs 46 slide over barbs 48 so that parts 10 and 32 are joined to one another nondetachably but axially displaceably; barbs 46, 48 form a stop in the proximal direction, as depicted in FIG. 2, and grooves 44 coact with the complementary projections 45 to provide rotation prevention for first cap 32, so that the latter cannot rotate relative to hollow needle carrier 10.

Figure 2:
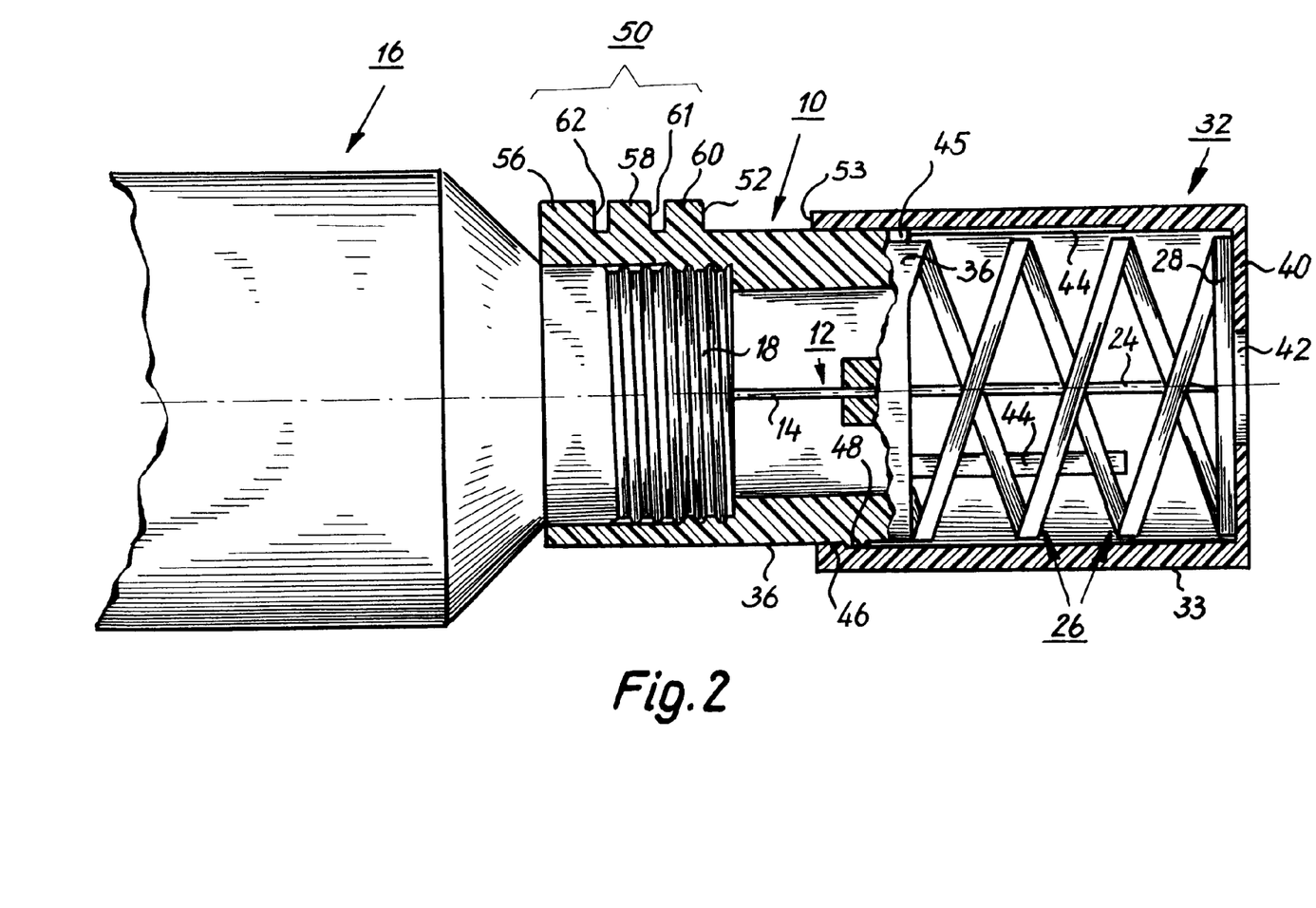
FIG. 2 shows a view similar to that of FIG. 1 but in the assembled state, the hollow needle being concealed by the arrangement.
Figure 3:
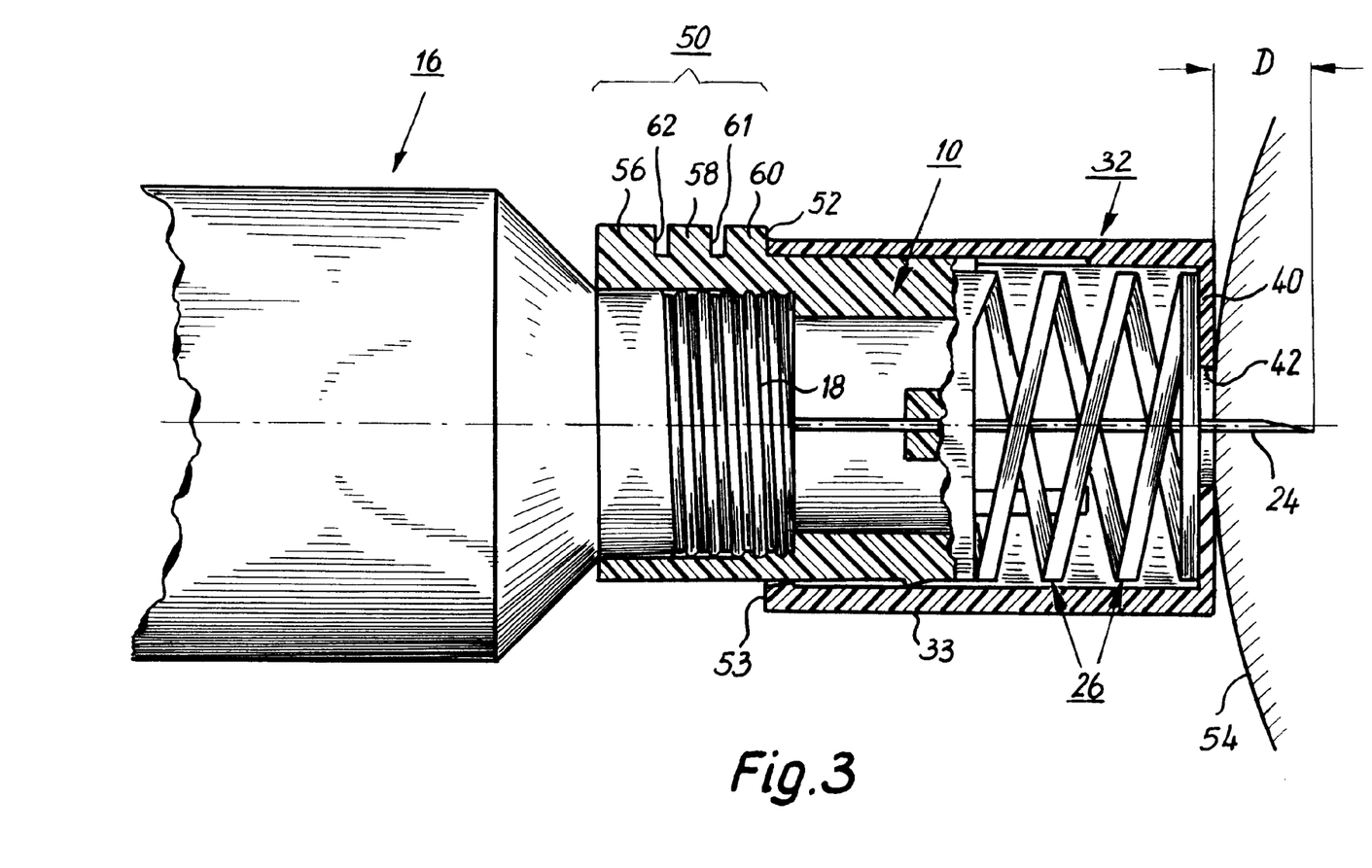
FIG. 3 shows a view similar to that of FIG. 2 but with the needle thrust in, the penetration depth being labeled D.

As clearly shown in FIGS. 1 through 3, there is located on outer circumference 36 of hollow needle carrier 10 a stop arrangement 50 against whose proximal shoulder 52 (as shown in FIG. 3) first cap 32 comes to rest with its distal end 53 when hollow needle 12 is thrust with its proximal end 24 into a body part 54 (indicated only schematically).

Figure 10:
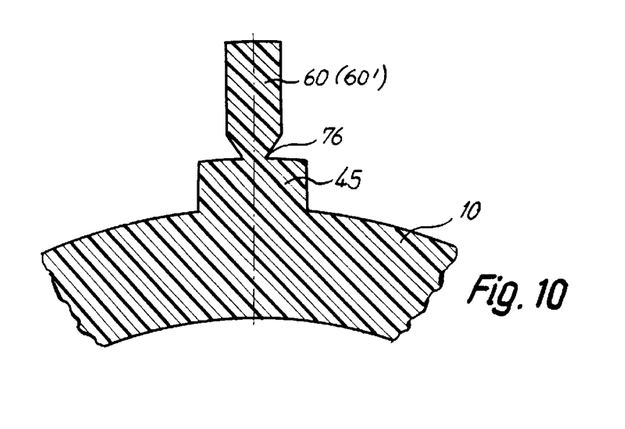
FIG. 10 is a sectional view through a defined breakpoint for a stop element, viewed along line C—C of FIG. 7.

Stop arrangement 50 has here a distal stop element 56, a central stop element 58, and a proximal stop element 60. At least proximal stop element 60 and central stop element 58 are each joined integrally to hollow needle carrier 10 by way of a defined break point 76 (FIG. 10), and consequently can be broken off from hollow needle carrier 10 by the user. This increases insertion depth D (FIG. 3) of the proximal hollow needle portion 24. Thus either it is possible to break off only stop element 60, so that first cap 32 then comes Lo rest against a shoulder 61 when hollow needle 12 is thrust in; or both stop elements 58 and 60 can be broken off, in which case first cap 32 then comes to rest against a shoulder 62 when hollow needle 12 is thrust in. In the latter case, the maximum penetration depth is attained.

Figure 4:
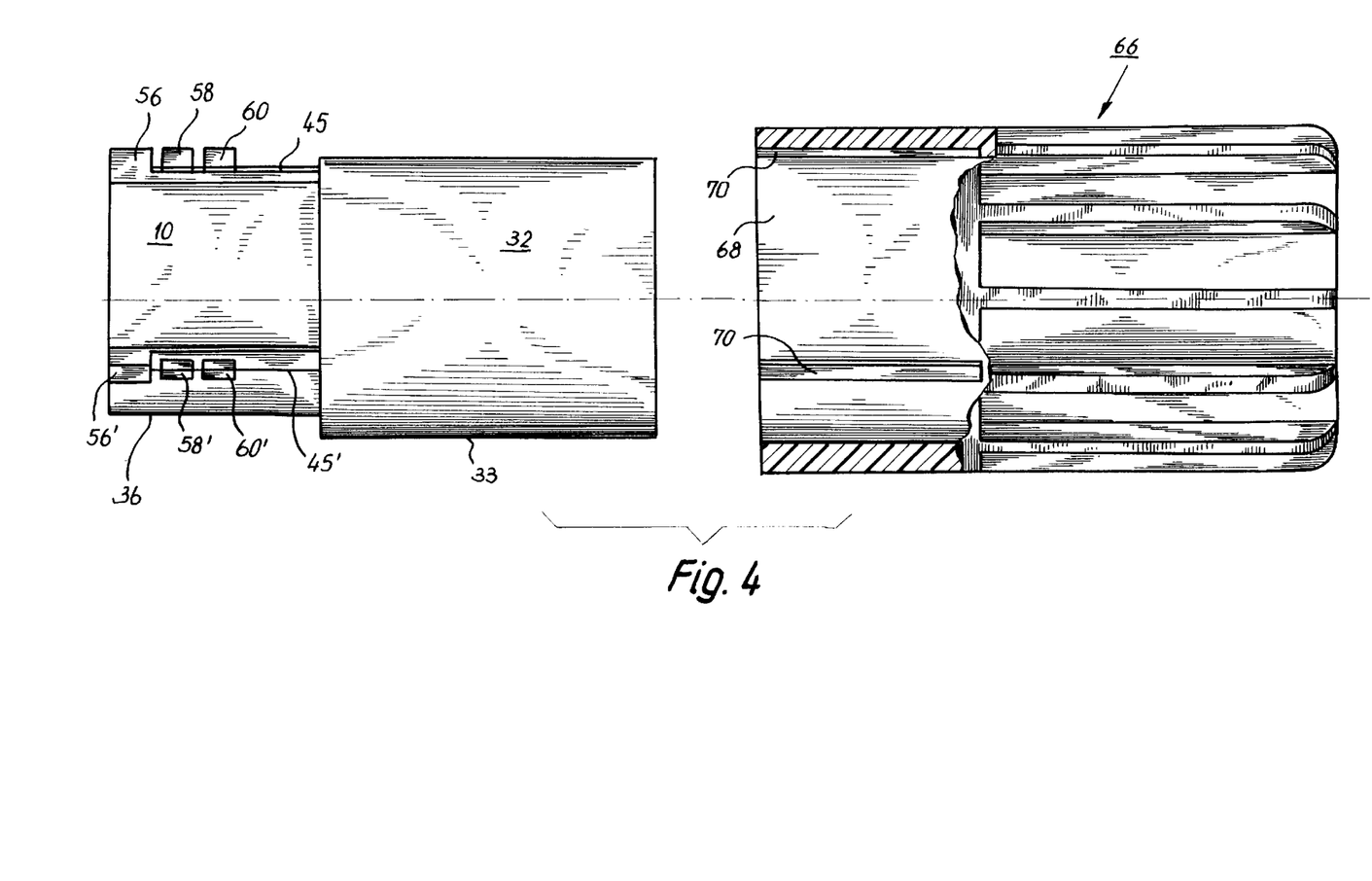
FIG. 4 shows a view similar to that of FIG. 2, additionally depicting an outer covering cap 66 which serves to encase the needle arrangement in sterile fashion.

FIG. 4 shows, at left, hollow needle carrier 10 on whose circumference stop elements 56, 58, 60 and 56, 58', 60, 56", etc. are arranged at uniform spacings of 120°. FIG. 6 shows the three stop elements 56, 56', and 56" in a plan view according to arrow VI of FIG. 5.

FIG. 4 shows that an outer covering cap 66, which provides sterile covering of the needle arrangement, is also provided. Outer covering cap 66 is depicted in FIG. 4 partially in longitudinal section, and it is evident that its cylindrical inner recess 68, which in the case of the complete needle arrangement shown in FIGS. 5 and 6 is slid over the cylindrical outer side 33 of first cap 32, has three longitudinal grooves 70 which are distributed uniformly on the circumference of inner recess 68 and are dimensioned such that they can be slid over stop elements 56, 58, 60, 56', 58', 60', 56" etc., as is particularly clearly evident from FIG. 6.

Figure 5:
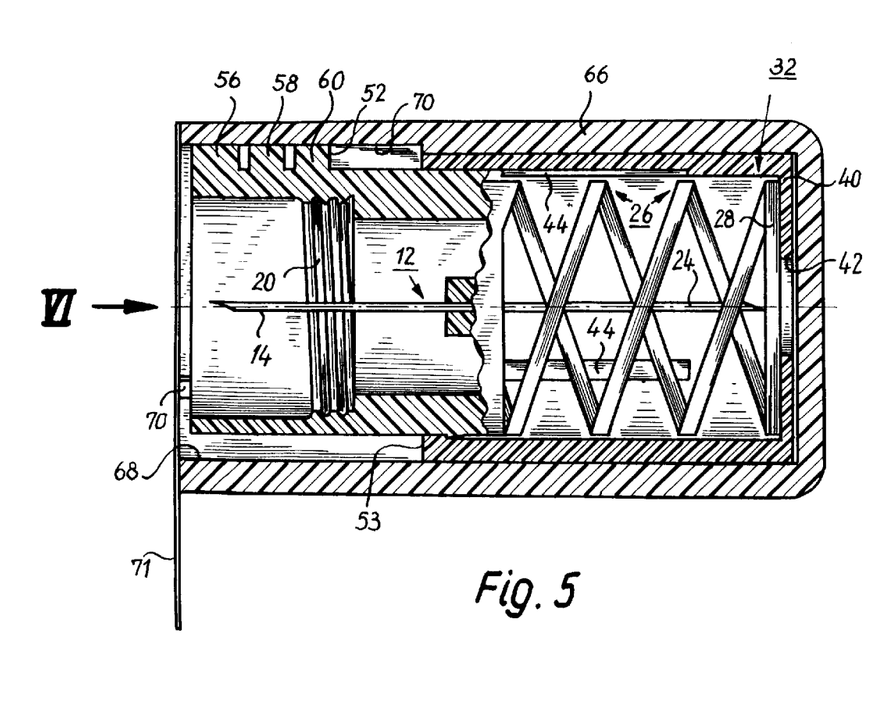
FIG. 5 shows a view of a complete, packaged needle arrangement according to a preferred embodiment of the invention.
Figure 6:
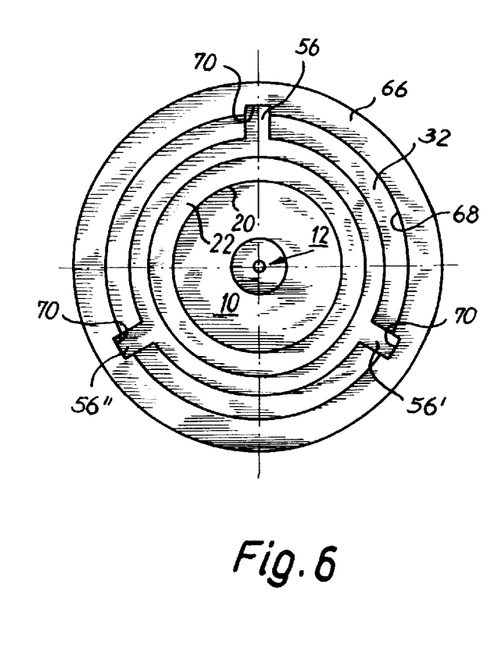
FIG. 6 is a plan view looking in the direction of arrow VI of FIG. 5.

FIG. 5 also shows a protective film 71 with which, in the complete needle arrangement, the opening (FIG. 5, left) of outer covering cap 66 can be sealed in sterile fashion. This film is welded on or adhesively bonded on, and is torn off before use. Film 71 is not depicted in FIG. 6.

Figure 7:
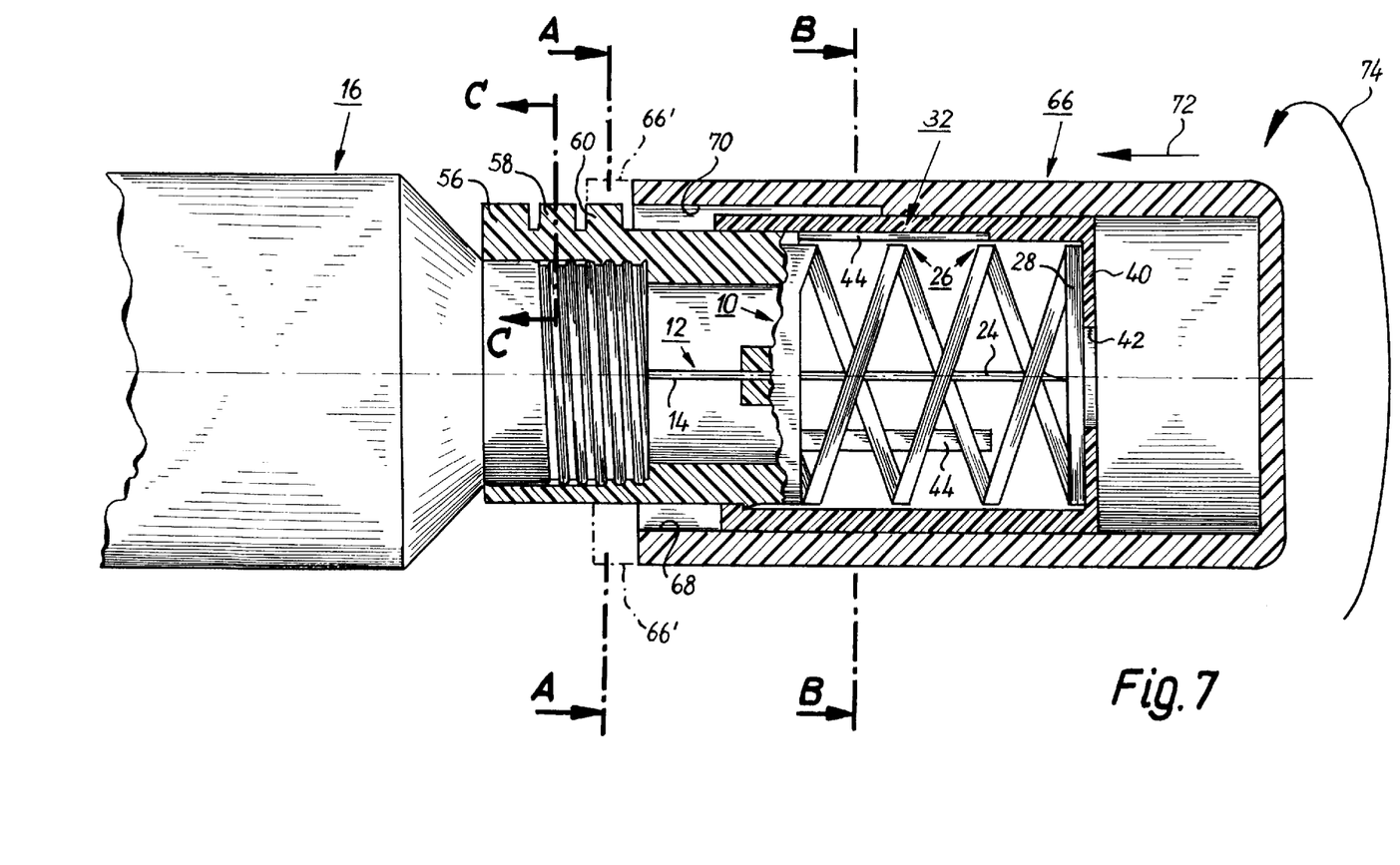
FIG. 7 is a view showing the adjustment of the penetration depth by way of the external covering cap 66.
Figure 8:
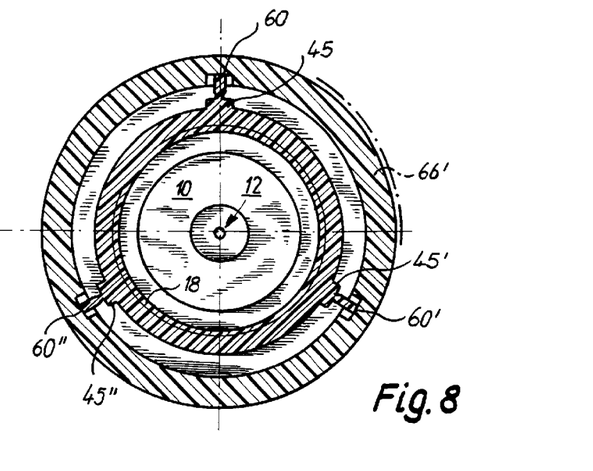
FIG. 8 is a sectional view along line A—A of FIG. 7.
Figure 9:
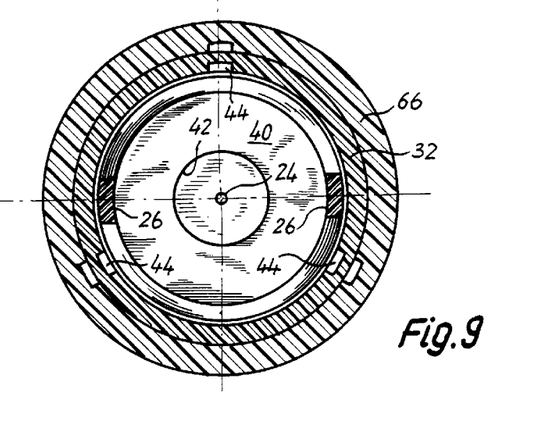
FIG. 9 is a sectional view along line B—B of FIG. 7.

FIG. 7 shows how outer covering cap 66 can be slid axially onto first cap 32 in the direction of arrow 72, arriving at a position 66' which is indicated in FIG. 7 with dot-dash lines and is depicted in section in FIG. 8, and in which its longitudinal grooves 70 are in engagement with stop elements 60, 60', 60". If outer covering cap 66 is then rotated in the direction of rotation arrow 74 depicted in FIG. 7, stop elements 60, 60', 60" are broken off along their defined break points 76 (cf. FIG. 10), i.e. penetration depth D (FIG. 3) is correspondingly increased in the manner already described above. In the same manner, it is also possible to break off both stop elements 58, 60 (correspondingly 58', 60', etc.), and thereby to increase penetration depth D even further.

What is described is thus a needle arrangement for an injection device 16. It has a hollow needle carrier 10 on which a hollow needle 12 is mounted and which is configured for detachable mounting on injection device 16. The arrangement has a cap 32 that is arranged on hollow needle carrier 10 displaceably approximately parallel to the longitudinal extension of hollow needle 12, is equipped at its proximal end segment with a passthrough opening 42 for hollow needle 12, and in its proximal end position substantially conceals hollow needle 12. A compression spring 26 is arranged between hollow needle carrier 10 and cap 32 in order to displace cap 32 into its proximal end position. Also provided is a covering cap 66 which surrounds the displaceable cap 32, hollow needle 12, and hollow needle carrier 10, and on its open side is sealed in sterile fashion by a tear-off sealing member 71. A needle arrangement of this kind can easily be replaced after an injection. It improves compliance because the patient does not at any time see hollow needle 12. The compression spring can be configured as plastic spring 26. It is preferably integral with hollow needle carrier 10, which simplifies manufacture.

Many other variants and modifications are, of course, also possible within the scope of the present invention.

What is claimed is:

1. A needle arrangement for an injection device (16),
    having a hollow needle carrier (10) on which a hollow needle (12) is mounted and which is configured for mounting on an injection device (16);
    having a first cap (32) which is arranged on the hollow needle carrier (10) and is displaceable approximately parallel to the longitudinal extension of the hollow needle (12) between a distal and a proximal end position, is formed at its proximal end segment with a passthrough opening (42) for the hollow needle (12), and in its proximal end position substantially conceals the hollow needle (12);
    having a compression spring (26), arranged between the hollow needle carrier (10) and the first cap (32), for displacing the first cap (32) into its proximal end position;
    having a second cap (66) adapted to surround said displaceable first cap (32), said hollow needle (12) and said hollow needle carrier (18), and having a user-removable protective barrier (71) closing off an open side of said second cap, whereby said second cap (66) and said protective barrier together form a sterile enclosure around said first cap (32), said hollow needle (12) and said needle carrier (10).

2. The needle arrangement as defined in claim 1, wherein said hollow needle carrier (10) is formed with an internal thread (20) for engagement with an external thread (18) formed on a surface of an associated injection device (16).

3. The needle arrangement as defined in claim 1, wherein said cover cap (66) has a form adapted for transfer of torque to said hollow needle carrier (10).

4. The needle arrangement as defined in claim 3, wherein said cover cap (66) is shaped for form-locking engagement with said hollow needle carrier (10).

5. The needle arrangement according to claim 1, wherein said user-removable protective barrier (71) is a peelable foil bonded across said open side of said second cap (66).

6. The needle arrangement according to claim 1, wherein an outer surface (36) of said hollow needle carrier (10) is formed with at least two stop elements (58, 60, 58', 60') serving to limit axial displacement of said first cap (32), said stop elements being frangible from said needle carrier at respective breakpoints (76) formed therein.

7. The needle arrangement according to claim 6, wherein the cover cap (66) has a form adapted to influence at least one stop member (58, 60, 58', 60') formed on an outer surface of said hollow needle carrier (10) in order to set a penetration depth (D) of said needle.

8. The needle arrangement as defined in claim 7, wherein the at least one stop member (58, 60) is mounted on the hollow needle carrier (10) via a defined breakpoint (76) at which said stop member can be broken off by a rotational motion (74) of the covering cap (66, 66') brought into engagement with said stop member.

9. The needle arrangement as defined in claim 6, wherein said breakpoint serves as a axial guide for displacement of said first cap (32) relative to said hollow needle carrier (10).

10. The needle arrangement according to claim 1, wherein the first cap (32) is arranged displaceably on a substantially cylindrical circumferential surface (36) of the hollow needle carrier (10), and a rotation preventer (44, 45) is provided between the hollow needle carrier (10) and the first cap (32).

11. The needle arrangement according to claim 10, wherein said rotation preventer includes a longitudinal groove (44), formed on one of said first cap (32) and said needle carrier (10), and a complementary projection (45), adapted to engage in said groove (44), formed on the other of said first cap (32) and said needle carrier (10).

12. The needle arrangement according to claim 1, wherein said compression spring (26) is formed of plastic material.

13. The needle arrangement as defined in claim 12, wherein said plastic spring is formed integrally with said needle carrier (10).

14. The needle arrangement according to claim 12, wherein said plastic spring (26) has a proximal end formed as a ring (32), said ring engaging against said first cap (32) and urging said cap in a proximal direction.

15. The needle arrangement as defined in claim 14, wherein the ring (28) is formed integrally with said plastic spring (26).

16. The needle arrangement as defined in claim 12, wherein the plastic spring (26) includes a pair of helical spring elements (26a, 26b), each formed integrally with said hollow needle carrier (10).

\* \* \* \* \*